US011246529B2

(12) United States Patent
Fang

(10) Patent No.: US 11,246,529 B2
(45) Date of Patent: Feb. 15, 2022

(54) METHOD TO LOCALIZE SMALL AND HIGH CONTRAST INCLUSIONS IN ILL-POSED MODEL-BASED IMAGING MODALITIES

(71) Applicant: Northeastern University, Boston, MA (US)

(72) Inventor: Qianqian Fang, North Reading, MA (US)

(73) Assignee: Northeastern University, Boston, MA (US)

(*) Notice: Subject to any disclaimer, the term of this patent is extended or adjusted under 35 U.S.C. 154(b) by 392 days.

(21) Appl. No.: 16/512,164

(22) Filed: Jul. 15, 2019

(65) Prior Publication Data

US 2020/0015744 A1 Jan. 16, 2020

Related U.S. Application Data

(60) Provisional application No. 62/697,740, filed on Jul. 13, 2018.

(51) Int. Cl.
*A61B 5/00* (2006.01)
*A61B 5/1455* (2006.01)
*A61B 5/0536* (2021.01)
*A61B 5/107* (2006.01)
*A61B 5/01* (2006.01)

(52) U.S. Cl.
CPC .......... *A61B 5/4887* (2013.01); *A61B 5/0042* (2013.01); *A61B 5/0073* (2013.01); *A61B 5/0091* (2013.01); *A61B 5/015* (2013.01); *A61B 5/0536* (2013.01); *A61B 5/1075* (2013.01); *A61B 5/1079* (2013.01); *A61B 5/14553* (2013.01); *A61B 5/4872* (2013.01); *A61B 5/4875* (2013.01); *A61B 5/6898* (2013.01); *A61B 5/7425* (2013.01)

(58) Field of Classification Search
CPC ... A61B 5/4887; A61B 5/0042; A61B 5/0073; A61B 5/0091
See application file for complete search history.

(56) References Cited

U.S. PATENT DOCUMENTS

| 10,885,680 | B2* | 1/2021 | Noguchi | A61B 6/5205 |
| 2010/0128958 | A1* | 5/2010 | Chen | G06T 11/006 |
| | | | | 382/132 |
| 2020/0260960 | A1* | 8/2020 | Zhu | G16H 30/40 |

OTHER PUBLICATIONS

Deng B, Brooks D H, Boas D A, et al. "Characterization of structural prior guided optical tomography using realistic breast models derived from dual energy x-ray mammography" Biomedical Optics Express. 6(7): 2366-79 (2015).

(Continued)

*Primary Examiner* — Joseph M Santos Rodriguez
(74) *Attorney, Agent, or Firm* — Hamilton, Brook, Smith & Reynolds, P.C.

(57) ABSTRACT

A detector and inclusion location method that uses a reconstruction technique to target and localize sparse small-sized but high-contrast objects, such as a tumor inside tissue. The reconstruction technique applied, can dramatically enhance the property contrast of the tumors or abnormal inclusions by ten to one hundred fold. The reconstruction technique enables the use of nonlinear imaging ill-posed techniques that are function-oriented imaging techniques without any need for structural prior knowledge.

20 Claims, 8 Drawing Sheets

(56) References Cited

OTHER PUBLICATIONS

American Cancer Society, "Cancer Facts and Figures 2015", American Cancer Society, 2015.
Harris, et al, "Medical progress: Breast cancer", NEJM, 327(9):319-328, 1992.
Cerussi, et al, "Sources of absorption and scattering contrast for near-infrared optical mammography", Acad. Radiol., 8:209-210, 2001.
Poplack, et al, "Electromagnetic breast imaging: results of a pilot study in women with abnormal mammograms", Radiology, 243:350-359, 2007.
Zhu, et al, "Imaging tumor angiogenesis by use of combined nearinfrared diffusive light and ultrasound", Opt. Lett., 28:337-339, 2003.
Ntziachristos, et al, "Mri-guided diffuse optical spectroscopy of malignant and benign breast lesions", Neoplasia, 4:347-354, 2002.
Brooksby, et al, "Imaging breast adipose and fibroglandular tissue molecular signatures by using hybrid mri-guided near-infrared spectral tomography", Proc. Natl. Acad. Sci. U.S.A., 103:8828-8833, 2006.
Carpenter, et al, "Methodology development for three-dimensional mr-guided near infrared spectroscopy of breast tumors", Opt. Express., 16:17903-17914, 2008.
Zhang, et al, "Coregistered tomographic x-ray and optical breast imaging: initial results", J. Biomed. Opt., 10, 2005.
Fang, et al, "Combined optical imaging and mammography of the healthy breast: Optical contrast derived from breast structure and compression", IEEE Trans. Med. Imaging, 28:30-42, 2009.
Fang, et al, "Compositional-prior-guided image reconstruction algorithm for multi-modality imaging", Biomedical Optics Express, 1:223-235, 2010.
Taroni, et al, "Time-resolved optical mammography between 637 and 985 nm: clinical study on the detection and identification of breast lesions", Phys. Med. Biol., 50:2469-2488, 2005.
Enfield, et al, "Three-dimensional time-resolved optical mammography of the uncompressed breast", Appl. Opt., 46:3628-3638, 2007.
Choe, et al, "Differentiation of benign and malignant breast tumors by in-vivo three-dimensional parallel-plate diffuse optical tomography", J. Biomed. Opt., 14, 2009.
Zhu, et al, "Early-stage invasive breast cancers: potential role of optical tomography with us localization in assisting diagnosis", Radiology, 243:350-359, 2007.
Fang, et al, "Combined optical and x-ray tomosynthesis breast imaging", Radiology, vol. 258: No. 1—Jan. 2011.
Cerussi, et al, "Predicting response to breast cancer neoadjuvant chemotherapy using diffuse optical spectroscopy", Proc. Natl. Acad. Sci. U.S.A., 104:4014-4019, 2007.
Choe, et al, "Diffuse optical tomography of breast cancer during neoadjuvant chemotherapy: A case study with comparison to mri", Med. Phys., 32:1128-1139, 2005.
Jacques, "Corrigendum: Optical properties of biological tissues: a review", Phys. Med. Biol. 58 (2013) 5007-5008, 27 pp.
Carp, et al, "Diffuse Optical Imaging", Pathobiology of Human Disease: A Dynamic Encyclopedia of Disease Mechanisms, 3925-3942, 2014.

Vaupel, et al, "Blood flow, oxygen and nutrient supply, and metabolic microenvironment of human tumors: A review", Cancer Research, 49:6449-6465, 1989.
Gu, et al, "Differentiation of cysts from solid tumors in the breast with diffuse optical tomography", Acad Radiol., 11:53-60, 2004.
Jiang, "Diffuse Optical Tomography: Principles and Applications", 2010, Chapter 1, 7 pages.
Gandjbakhche, et al, "Resolution limits for optical transillumination of abnormalities deeply embedded in tissues", Med. Phys., 21:185-191, 1999.
Choe, et al, "Diffuse Optical Tomography of the Breast", Emerging Technology in Breast Imaging and Mammography, Chapter 18, American Scientific Publishers, 317-342, 2008.
Wu, et al, "Digital tomosynthesis mammography using a parallel maximum-likelihood reconstruction method" Proc. SPIE, 5368:1-11, 2004.
Helvie, "Digital mammography imaging: Breast tomosynthesis and advanced applications", Radiol Clin North Am., 48:917-929, 2010.
Brooksby, et al, Combining near-infrared tomography and magnetic resonance imaging to study in vivo breast tissue: implementation of a laplacian-type regularization to incorporate magnetic resonance structure, J. Biomed. Opt., 10, 2005.
Li, et al, "Tomographic optical breast imaging guided by threedimensional mammography", Appl. Opt., 42:5181-5190, 2003.
Wu, et al, "Tomographic mammography using a limited number of low-dose conebeam projection images:", Med. Phys., 30:365-380, 2003.
Yalavarthy, et al, "Structural information within regularization matrices improves near infrared diffuse optical tomography", Opt. Express, 15:8043-8058, 2007.
Grosenick, et al, "Time-domain scanning optical mammography: I. Recording and assessment of mammograms of 154 patients", Phys. Med. Biol., 50:2429-2449, 2005.
Thrall, "Look Ahead: The Future of Medical Imaging," RSNA News Aug. 2015.
Yu, et al, "Scalable and massively parallel Monte Carlo photon transport simulations for heterogeneous computing platforms," J. Biomed. Opt. 23(1), 010504 (2018).
Yuan, et al, "Graphics processing units-accelerated adaptive nonlocal means filter for denoising three-dimensional Monte Carlo photon transport simulations", Journal of Biomedical Optics 23(12), 121618 (Dec. 2018).
Debakla, et al, "MRI Image Denoising Approach based on TV and Neural Network Filter", 2015.
D'Andrea, et al, "Fast 3D optical reconstruction in turbid media using spatially modulated light", Biomedical Optics Express. 1(2): 471-481 (2010).
Xu, et al, "Computer-automated detection of unknown breast lesions using functional optical imaging," Rad. Soc. of North America (RSNA) Paper#BR235-SD-TUA3, Chicago, IL, 2017.
Fang, et al, "Singular Value Analysis of the Jacobian Matrix in Microwave Image Reconstruction", IEEE Transactions on Antennas and Propagation, vol. 54, No. 8, Aug. 2006.
Taroni, et al, "Seven-wavelength time-resolved optical mammography extending beyond 1000 nm for breast collagen quantification", Sep. 2010, vol. 1, No. 2, Biomedical Optics Express 471.

* cited by examiner

METHOD TO LOCALIZE SMALL AND HIGH CONTRAST INCLUSIONS IN ILL-POSED MODEL-BASED IMAGING MODALITIES

RELATED APPLICATION

This application claims the benefit of U.S. Provisional Application No. 62/697,740, filed on Jul. 13, 2018. The entire teachings of the above application(s) are incorporated herein by reference.

BACKGROUND

Modern medical imaging has gradually evolved from structure-oriented imaging modalities, such as x-ray, CT, and structural-MM imaging, to multi-modal diagnosis incorporating function-oriented imaging techniques, such as positron emission tomography (PET), diffuse optical tomography (DOT), microwave tomography (MWT), and electrical impedance tomography (EIT), ultrasound elastography, etc. These new and emerging techniques focus on probing tissue functional parameters, such as optical, dielectric, thermal, mechanical characteristics, and correlate those with tissue physiologies and disease pathology. The hope of these methods lies in the fact that many of the functional parameters show significant contrast, sometimes on the order of 10 to 100 fold, between the diseased tissue and the normal tissue.

While these imaging techniques are increasingly used in research, have shown promise for disease-specificity, are safe-to-use, non-invasiveness and low-cost, their clinical presence remains very limited. A major reason for the slow adoption of these methods is the low-spatial image resolution. Most of these imaging techniques utilize non-linear and model-based reconstructions—by solving a nonlinear partial differential equation (in DOT—diffusion equation or radiative transfer equation, in MWT, the Maxwell or Helmholtz equation etc.). The image reconstruction problems, i.e. the inverse problems, for most of these techniques are known to be "ill-posed": that means the measurements from such modalities contain intrinsic redundancy, making the solution severely and intrinsically sensitive to noise present in the data. Therefore, in order to make these imaging modalities produce stable images, one must apply a technique called "regularization" to convert the "μl-posed" inverse problem into a "well-posed", solvable problem. However, a common result of such regularization method is the loss of the spatial details of the images. Therefore, the majority of the aforementioned nonlinear imaging techniques can only produce low-spatial resolution images. For example, in many published DOT studies, one can only reliably recover tumors about 1 cm in diameter in deep tissue (such as a breast), similar in microwave imaging and EIT. Typically, the deeper the inclusion, the lower the resolution that can be achieved.

Because of the loss of spatial resolution, prior art methods cannot use optical images recovered from DOT, or dielectric images from MWT/EIT to localize unknown tumors, especially small tumors. Instead, the majority of prior art methods are focused on characterizing lesions at known locations, determining whether it is benign or malignant, or whether it has responded to treatment or not. Due to the excessive smoothing effect of the regularization, the recovered tissue contrast is typically much lower than the anticipated contrast obtained from ex vivo measurements; the contrast loss is even more significant in small-sized inclusions.

The slow clinical adoption of nonlinear ill-posed imaging modalities is largely a result of a desire to reconstruct high spatial resolution images "uniformly" across the entire imaging domain, regardless it is within the diseased tissues or normal tissues. The ill-posedness of the associated inverse problem is a result of intrinsic redundancy among the measurement data. In order words, the more measurements are taken, the less "independent" information is gained. Even if it is possible to take millions of data points from these systems, the "effective" independent measurements account only a very small fraction, perhaps on the scale of a few thousands, indicated by the "effective rank" of the inversion matrix (or the Jacobian). If a reconstruction is performed for a high uniform resolution image containing millions of independent unknowns using only a low-rank inversion matrix, it directly leads to a severely underdetermined problem, which can only be solved by sacrificing high-spatial information using regularizations as in prior art methods.

On the other hand, for the majority of the applications, the goal is not limited to producing high spatial functional images across the entire imaging domain, but rather to find and characterize limited number of deeply-embedded and small-sized abnormalities that are known to have relatively high functional contrast, such as finding a single small breast cancer several centimeters inside the human breast, or localizing a brain activation in the brain cortex using optical or electromagnetic data acquired on the scalp surface. A high spatial detailed functional image is not always required in order to make clinically relevant diagnosis. A need exists for the ability to accurately find and recover the locations and contrasts of a small number (i.e. sparse) of localized and high-contrast abnormalities, such as a single tumor or multi-foci tumors, within deep tissue using nonlinear functional imaging modalities.

A need exists for a reconstruction technique that is specifically targeted to image sparse, small-sized but high-contrast objects, such as the tumor inside tissue. A further need exists to have a technique to enhance the property contrast of the tumors or abnormal inclusions without knowing the location of the tumor prior to imaging.

SUMMARY

The location of an inclusion is determined in a method comprising creating, using a functional imaging technique, a map of physiological properties of the tissue area, wherein the tissue area is composed of the inclusion and background tissue. An inclusion profile is determined based upon physiological properties of the inclusion, the physiological properties of the inclusion being distinct from physiological properties of the background tissue. The inclusion profile may include inclusion shape. The map of physiological properties of the tissue area is divided into regions. For each region, creating a map of surrogate metrics wherein the surrogate metrics are derived from physiological properties of the tissue area calculated by applying a reconstruction using the inclusion profile as hypothesized known values of physiological properties of tissue within the region. In one embodiment the reconstruction model is regularized Gauss-newton reconstruction. Finally, the location of the inclusion is determined based upon the map of surrogate metrics of the tissue area. The determining the location of the inclusion can be accomplished without any structural images or structural information. In some embodiments the nature of the inclusion is also characterized and the shape, size and orientation are determined based on the maps of surrogate metrics of the tissue area.

The functional imaging technique may be an ill-posed imaging technique utilizing model-based reconstructions. The ill-posed imaging technique can be diffuse optical tomography.

The physiological properties of tissue area can include at least one of oxyhemoglobin concentration, deoxyhemoglobin concentration, total hemoglobin concentration, oxygen saturation, water concentration, lipids concentration, absorption coefficient, and reduced scattering coefficient.

Determining the location of the inclusion may further include creating a contrast map, the contrast map displaying, at each region, variation between the map of surrogate metrics of the tissue area derived from physiological properties of the tissue area calculated using the inclusion profile as a hypothesized known value of physiological properties of the tissue within the region and the map of physiological properties of the tissue area. In such embodiments, a region containing the inclusion has a variation over ten time greater than a region not containing the inclusion.

A tissue abnormality detector that is comprised of an imaging system that creates, using a function orientation imaging technique, a map of physiological properties of a tissue area, wherein the tissue area is composed of the tissue abnormality and background tissue. The detector also has an input configured to receive a tissue abnormality profile that includes physiological properties of the tissue abnormality, the physiological properties of the tissue abnormality being distinct from physiological properties of the background tissue. And the detector has an analysis unit configured to divide the map of physiological properties of the tissue area into regions and create, for each region, a new map of physiological properties of the tissue area by applying a reconstruction using the tissue abnormality profile as hypothesized known values of physiological properties of tissue within the region; wherein a region containing the tissue abnormality can be identified based upon the new of physiological properties of the tissue area. Identifying the region containing the tissue abnormality can be accomplished without any structural images or structural priors. In some embodiments the tissue abnormality is a tumor. In such embodiments, malignancy of the tumor may be determined using one or a combination of the recovered contrast, shape, and size information The detector may additionally have an image output configured to integrate with a computer aided detection system to display the region containing the tissue abnormality. The image output can be further configured to display a contrast map, the contrast map displaying, at each region, variation between the new map of physiological properties of the tissue area created using the tumor profile as the hypothesized known value of physiological properties of the tissue within the region and the map of physiological properties of the tissue area.

The tissue area may be breast tissue, brain tissue, or any other tissue type desired by the user.

The detector may have the imaging system is located on a user's personal portable device.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1A:
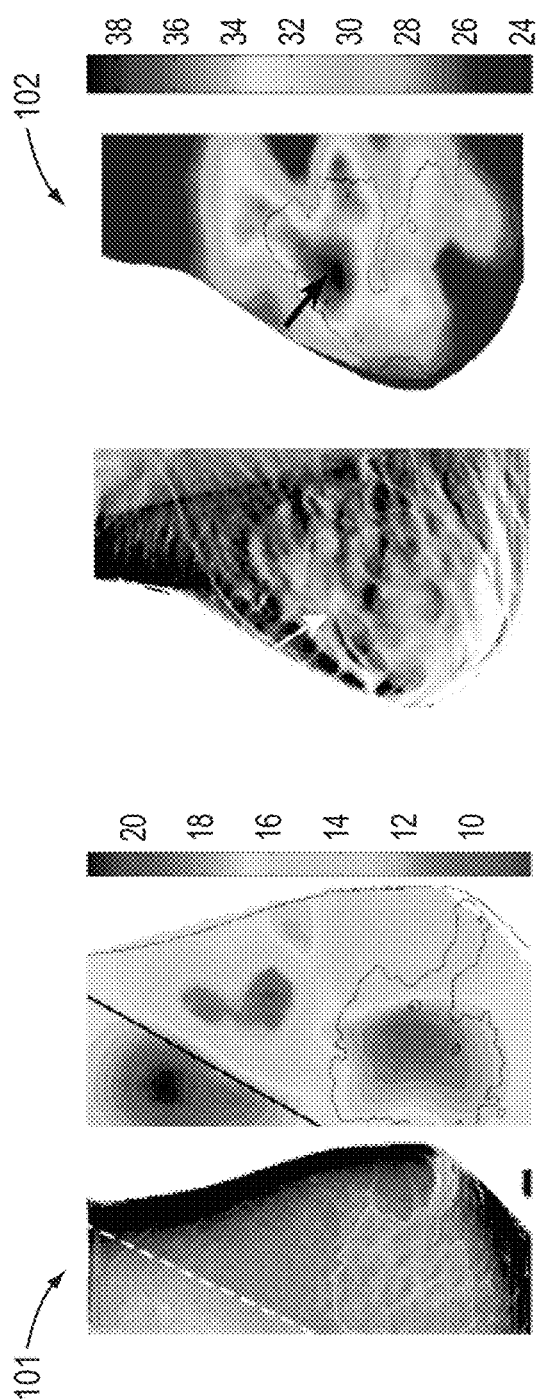
FIGS. 1a, 1b, and 1c are examples of prior art imaging methods with low spatial resolution.

A description of example embodiments follows.

Multi-modal breast imaging combining mammography with diffuse optical tomography (DOT) has been shown as a viable approach to address the poor positive predictive value (ppv) in standalone mammography. A structural-prior guided DOT reconstruction algorithm, fusing high-resolution x-ray tissue anatomy with functional optical measurements was developed and has been shown that accurate characterization of malignant and benign tumors is possible for lesions at known locations.

To localize breast lesions/tumors at unknown locations using DOT measurements is significantly more challenging compared to characterizing known lesions, because of the low-resolution nature of DOT image reconstructions. Prior art techniques for breast DOT, and other imaging methods, either standalone or combined with another modality, focus on characterizing known tumors. In applications where access to structural imaging systems is not possible, diagnosing and characterizing small and potential high-contrast tumors is quite challenging with only optical measurements (or other non-linear model-based imaging modalities, such as microwave tomography or electrical impedance tomography, where an ill-posed inverse problem is solved).

This invention includes an effective method to recover the location of unknown tissue abnormalities and/or inclusions in a tissue area using completely optical measurements without needing spatial priors. The tissue abnormalities can be tumors. The method can also be utilized with imaging techniques that measure dielectric, thermal, mechanical characteristics, or other physiological property of the tissue area. With this technique, it is possible to dramatically enhance the property contrast of the tumors or abnormal inclusions by 10 to 100 fold compared to the background or normal tissue. In prior art methods the property contrast is typically less than twofold. Additionally, the method can obtain high-contrast inclusion characterization based on low-sampling nonlinear imaging methods without any spatial priors. These can be displayed as an image of a tissue area with the values of the physiological properties displayed in a heat map.

Importantly, because this method does not require structural priors or co-registered structural (x-ray) images, it makes it possible to localize tumors only using positron emission tomography (PET), diffuse optical tomography (DOT), microwave tomography (MWT), electrical impedance tomography (EIT), and elastography etc. Nearly all ill-posed imaging technique can benefit from an embodiment of this invention. This enables the use of nonlinear imaging techniques, often known to be portable and low-cost, to spatially localize unknown tumors and characterize them without expensive, and large imaging systems. This method allows the use of optical tomography, along with many other non-linear imaging modalities, to image a lesion of unknown location with superior spatial accuracy and excellent contrast, with or without structural priors from another modality. The portability and low cost of diffuse optical tomography (DOT), microwave tomography (MWT), electrical impedance tomography (EIT), and other functional imaging techniques allow the method to use imaging data gathered by a cell-phone or other portable personal device to allow for monitoring tumor growth or treatment at home.

This method is effective in revealing a small and high-contrast inclusion, which is useful in tumor detection and other functional imaging scenarios, particularly early detection. This is different from the prior art methods which focus on recovering entire images without looking for specific image features. The method can also be used in other situations that involve the imaging/location of a small area with physiological properties distinct from the surrounding area. This includes, brain activation enhancement, fluorescence imaging in small animals, and intro-operative margin assessment.

Combined with computer algorithms, this method can be used to reliably find malignant tumors. Embodiments of this method can generate high-contrast tumor functional images based on low-cost DOT/MWT/EIT measurements. Combined with some simple image processing techniques, this can help automatically localize malignant tumors in a computer-aided-detection (CAD) procedure. The computer aided detection may allow for the finding suspicious tumors using only optical and functional imaging modalities. The method can be expanded to characterize other types of target features, such as the shape, size, and orientation of the inclusions.

This invention is capable of accurate recovery of the locations, contrasts, as well as other relevant properties, of embedded tissue abnormalities without needing to recover high uniform-spatial-resolution tissue property images. Instead of solving a model-based parameter estimation problem aiming at the recovery of tissue property maps of uniform resolution, this invention produces maps of surrogate metrics, derived from physiological properties of the tissue area generated by mathematically incorporating a hypothesized abnormality in each of the discretized spatial regions in the imaging domain. Such hypothesized abnormality can include not only the hypothesized location, but also hypothesized lesion sizes, orientations, contrasts, and other properties that are desired to be determined.

For each of the hypothetical locations, inclusion sizes, orientations, or other property dimensions of a target tissue abnormality or other object, at least one reconstruction is performed in which the hypothesized abnormality information or profile is mathematically incorporated. Additional reconstructions can be performed, such as those without incorporating the hypothesized abnormality information. These reconstructions produce new physiological images of the target domain. By mathematically processing these images, and extracting meaningful metrics that characterize the image features, such as the maximum difference or maximum variance of the difference in the entirety or portion of the image space, surrogate metrics are identified/created that specifically characterize the changes due to whether the hypothesized abnormality is incorporated or not. When a real tissue abnormality presents in the interrogated area with properties—locations, sizes, or contrasts—matching those of the hypothesized abnormality, the changes observed in the selected surrogate metrics are dramatically higher than the cases where no such abnormality exists in interrogated region or the abnormality does not match the hypothesized abnormality. By systematically scanning all hypothetical spatial locations and/or other abnormality property dimensions create maps of surrogate metrics are created and/or chosen to characterize variations in the physiological properties of the reconstructed images created for each hypothetical spatial location, sizes, contrasts, etc. From the maps of surrogate metrics, the location, size, contrast of one or multiple abnormalities can be determined. A real abnormality matching the hypothesized abnormality is likely exist to in regions where the surrogate metrics derived from the reconstructed physiological image are significantly different values then the surrogate metrics derived from the reconstructed physiological images of the surrounding regions. The spatial resolution of the surrogate metric images created is determined by the scanning step size of locations, and other property dimensions, and how accurate the hypothesized abnormality properties match those of the real abnormality and is not limited by the ill-posedness of the inverse problem of the imaging modality.

Figure 1C:
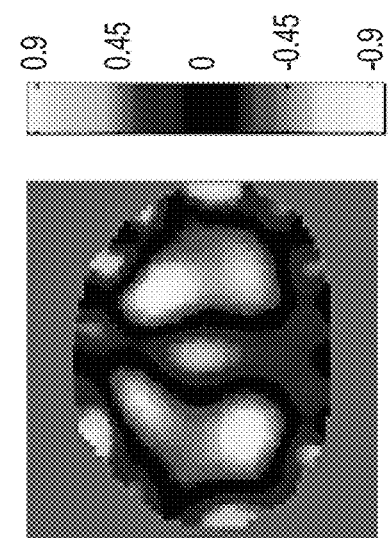
Figure 1B:
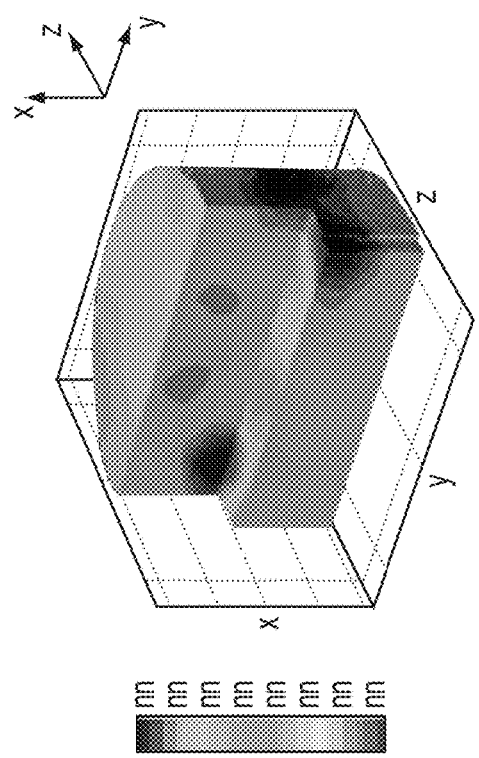

FIGS. 1a, 1b, and 1c are examples of prior art functional imaging methods with low spatial resolution. FIG. 1a includes sample DOT images next to an X-ray image of the same tissue area. The left set of images 101 shows normal breast tissue and the right set of images 102 shows breast tissue with a malignant tumor. The heat map of the DOT images correlate to optical physiological properties. These optical physiological properties may include absorption spectrum data correlated to oxy-hemoglobin (HbO) and deoxy-hemoglobin (HbR) concentration. Because a tissue abnormality, such as a tumor or inclusion, has different psychosocial properties than the surrounding background tissue, a tumor could be located by identifying an area of high contrast. However, FIG. 1a shows that the low resolution of optical images from DOT, without the application of the inventions method, are poorly suited to locating tumors. Despite the tumor being visible in the MM image, the lack of contrast and resolution in the DOT image prevents clear identification. FIG. 1b is a sample MWT image and FIG. 1c is a sample EIT image. All prior art imaging techniques, without the application of the present method, suffer from the same lack of resolution and are severely and intrinsically sensitive to noise present in the data. They cannot be used to clearly identify a tumor or inclusion that could be as small 5 mm.

Traditionally, the lack of resolution and contrast has been overcome by using reconstruction based on structural priors. Knowledge of tissue physiological properties, usually obtained through structural imaging such as radiography, provides an initial location guess and tissue composition constraints for image reconstruction. Within the scope of a breast cancer screening model, the tissue area can be defined as a combination of two tissue types—fibroglandular and adipose tissue, providing two-composition priors. Different priors can be determined for different tissue types and regions of interest. Using structural imaging, the physiological properties of the tissue types that proved the composition priors are established and the scattering amplitude and power calculated for all regions of the tissue area. For DOT reconstruction, the oxy-hemoglobin (HbO) deoxy-hemoglobin (HbR) and reduced scattering coefficient ($\mu_s'$) can be used and are linearly scaled to compute the absorption coefficient ($\mu_a$) and scattering amplitude of the tissue types and regions of the tissue area. For other imaging techniques, such as MWT and EIT, the relevant physiological properties are used to create the necessary structural priors. Additionally, the physiological properties and/or location of the tumor can be used as an additional prior. A reconstruction algorithm then uses the established priors to attempt to improve contrast differential of the original image.

Figure 2:
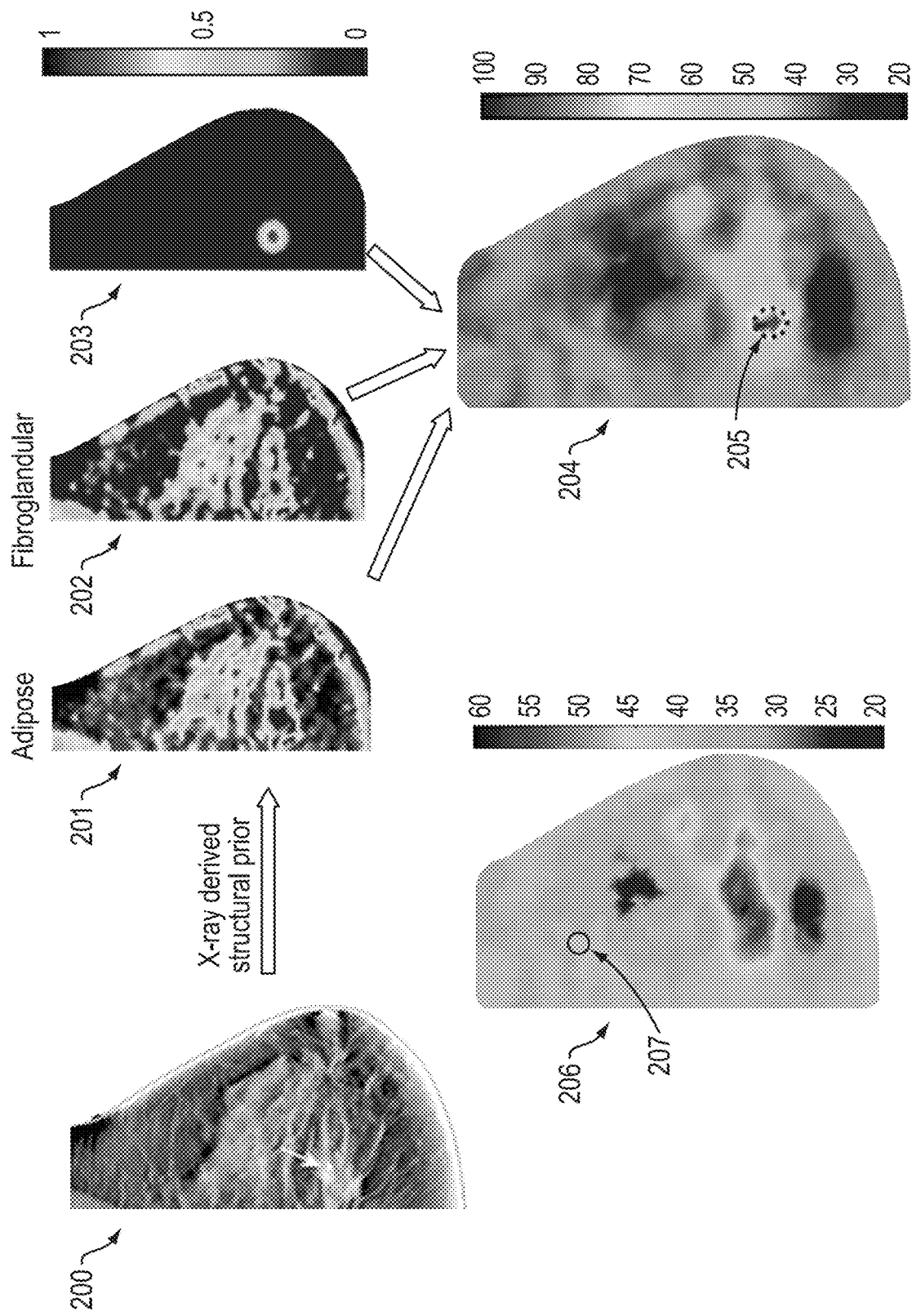
FIG. 2 is an example of a prior art reconstruction using structural priors and tumor location.

FIG. 2 is an example of a prior art reconstruction using structural priors and tumor location. X Ray image 200 is used to determine structural priors for the background tissue of the breast. The adipose prior is show is image 201 and the fibroglandular prior is shown in image 202. Additionally, a physician identified a suspicious tumor location shown in image 203. Using all three priors, a reconstruction of map of physiological properties of the tissue area 204 can be created with improved contrast and tumor location 205 clearly visible. While the method shown in FIG. 2. is useful, it requires information derived from X ray imaging and a presumed known tumor location. The prior art method of reconstruction using structural priors is discussed and explained in Fang, Q., Moore, R. H., Kopans, D. B. and Boas, D. A., *Compositional-prior-guided image Reconstruction Algorithm for Multi-modality Imaging*. Biomed. Opt. Express, 2010. 1(1), p. 223-35 which is incorporated by reference.

The reconstruction shown in FIG. 2 can be performed for any suspected tumor location as the third prior along with the structural priors for adipose and fibroglandular tissue. If a suspected tumor location does not correlate to actual tumor location, instead of producing a map with increased contrast such as map 204, the contrast does not improve significantly from the original image. Map 206 shows a reconstruction done with the tumor prior set at location 207 instead of at the correct tumor location 205.

The following method is described in detail with references to DOT imaging of optical physiological properties but can be applied to any ill-posed imaging technique such as MWT, EIT or PET imaging using the relevant imaged physiological properties. The following method is also described with references to tumor detection and localization in breast tissue, the invention can be applied to any region where there is a small inclusion within background tissue where the inclusion and background tissue have distinct physiological properties.

The invention includes a method that removes the requirement for any structural priors and performs reconstruction using only speculative tumor priors. This is accomplished, in part, by exploiting the different behavior of the reconstruction algorithm when the tumor prior is set at the correct location and when the tumor prior is set at the incorrect location as shown in maps 204 and 206. This location matching approach enhances change in contrast introduced by an inclusion when the location of the inclusion/tumor matches the hypothetical location. This behavior can be replicated using only a tumor prior.

To achieve this, the tissue area is imaged using a functional imaging technique such as DOT and the resulting image/map is parcellated into a search grid and compositional priors are generated for each region of interest. However, structural prior knowledge, based off X-ray imaging or other information source, is not included, leaving only one-composition prior consisting of tumor locations and physiological properties. The tissue area can be divided into two tissue types: 1) tumor tissue, and 2) non-tumor background tissue. A regularization matrix based on the two assumed tissue types can be created via a probability map, defined as a probability vector, $\{C_t(r), 1-C_t(r)\}$ at every spatial location r within the tissue area, where tumor prior ($C_t$) is a value between 0-1, denoting the probability (or volume fraction) of tumor tissue at that location. The tumor can be assumed anywhere in the tissue area. Because the method will dynamically interrogate every part of the tissue area by moving the hypothetical center of the tumor at all possible locations (or a subset), it is not necessary to know where is the true tumor location.

$C_t$ can be defined as a 3D Gaussian-sphere, but other types of probability profile are possible. Multiple shape templates can be used to not only localize the tumor but also determine its shape. Similar to potential location, the shape template that best matches the actual tumor shape will produce the most contrasting reconstruction.

The tissue area is divided into regions and each region of the domain is assigned a compositional vector $\{C_t(r), 1-C_t(r)\}$ that corresponds to the probability or volume fraction of tumor and non-tumor tissue types. The regions may be approximately 1 cubic centimeter. For every speculative tumor locations, the 3D physiological images of total hemoglobin concentration (HbT), oxygen saturation ($SO_2$) and the reduced scattering coefficient ($\mu_s'$) can be obtained by a reconstruction method, such as regularized Gauss newton reconstruction, using the hypothesized physiological properties of the tumor tissue as the values for the physiological properties at the speculative tumor location. The reconstruction produces suggested metrics that assume the physiological properties of the speculative tumor location match the presumed properties of the location. This can be done for the entire tissue area by performing a reconstruction with the hypothetical location of the tumor at each region of the tissue area. In other words, for each region a reconstruction will be performed where the only prior used is that of a tumor with the known or assumed tumor physiological properties within the reconstructed region.

When the assumed tumor matches the correct location of the actual tumor, a dramatic contrast will be generated between the reconstructed image and the original image; on the other side, when the assumed tumor does not match the correct tumor location, the image contrast enhancement is negligible. Surrogate metrics can be derived from the reconstructed physiological properties that highlight the contrast. By scanning all interested locations of the tumor using the speculated tumor Gaussian sphere, the reconstructed images changes can be combined to form a tumor feature-specific image. In some embodiments the tumor feature-specific image is created using the calculated/chosen surrogate metrics. The tumor feature-specific image may be a map showing the contrast between the reconstructed images, either the entire reconstructed image of physiological properties or calculated/chosen surrogate metrics, and the original image. Alternatively, the tumor feature-specific image may be created by performing the reconstruction method for each region simultaneously.

When the hypothesized location of the tumor profile matches the true location of the tumor, a dramatic enhancement in the contrast of the optical properties imaged occurs; on the other hand, when the hypothesized tumor profile moves away from the true tumor location, such enhancement diminishes quickly—the reconstructed image resembles the no-prior reconstructions with minimal changes. Such distinct response to concordant and discordant hypothesized tumor locations provides a way to automatically localize the unknown tumor. Tumor priors consisting of hypothetical tumor physiological properties are defied all possible locations using a search grid overlaid on the original image of the physiological properties of the tissue. For each hypothesized tumor location ($r_0$), an independent tumor prior $C_t(r_0)$ is generated and subsequently used in a 3-compositional DOT reconstruction resulting in one set of optical parameter maps (HbT(r, $\{C_t(r_0)\}$), $SO_2$(r, $\{C_t(r_0)\}$), and $\mu_s'(r,\{C_t(r_0)\})$). By subtracting the 2-compositional optical images by the baseline, i.e. the no-prior guided optical images $\mu_0(r)$, it can produce a differential optical image, $\Delta\mu(r,r_0)=\mu(r,\{C_t(r_0)\})-\mu_0(r)$, where $\mu$ can be HbT, $SO_2$ or $\mu_s'$.

Figure 3:
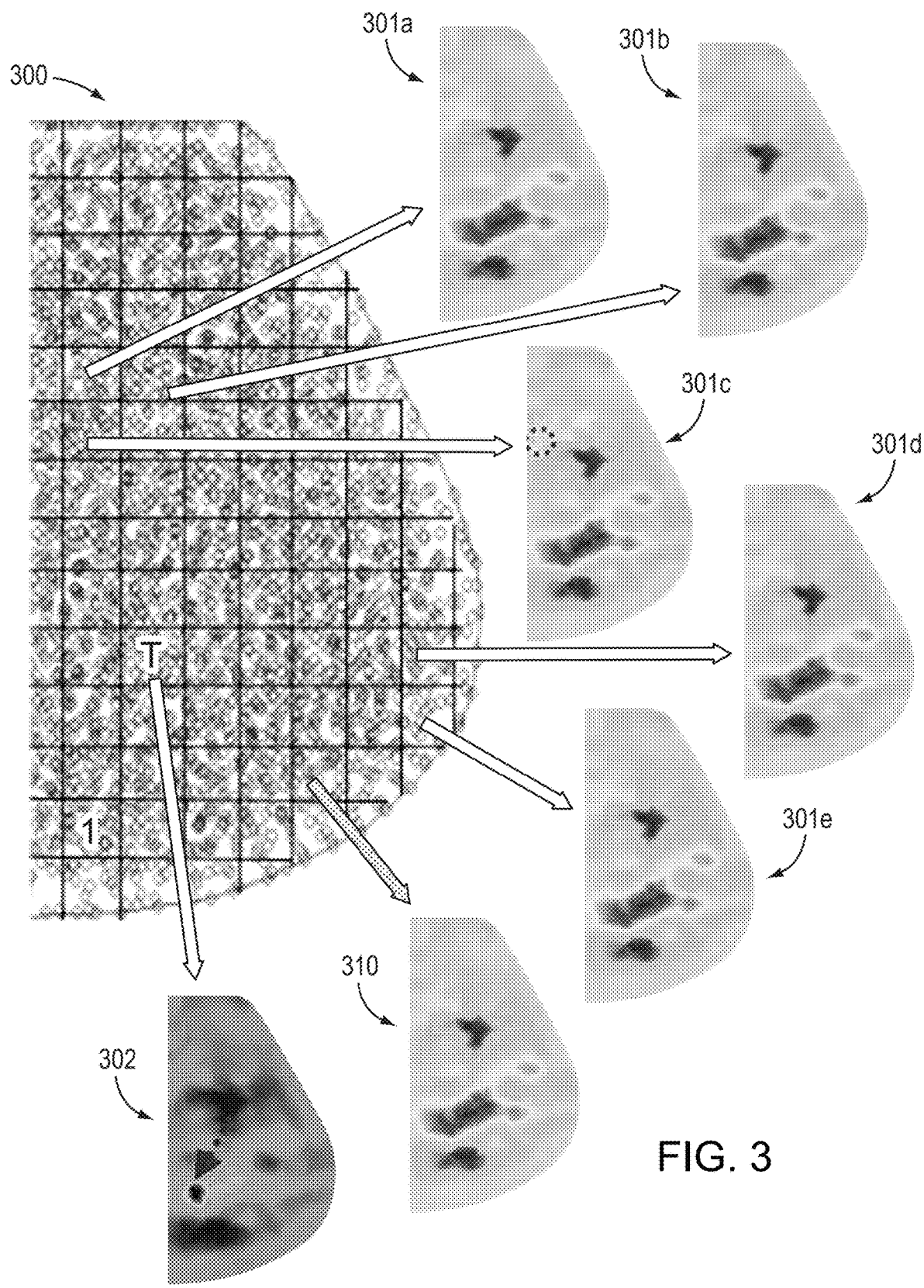
FIG. 3 is an example of the reconstructing an image of breast tissue using multiple hypothetical tumor location priors in accordance with the invention.

FIG. 3 is an example of the reconstructing an image of breast tissue using multiple hypothetical tumor location priors. Image 310 is a map of physiological properties of breast tissue obtained through an imaging technique such as DOT. Image 310 is a heat map but may be any other image type that can display varying data across an area. Image 310 may be 2-dimensional or 3 dimensional. Image 310 may be produced by known software such as Digibreast or other similar applications. Image 300 shows the division of the tissue area imaged into regions. For each region it is possible to perform a reconstruction to create a new image. The reconstructions are performed by using a prior that uses the physiological properties of a tumor/inclusion as the physiological properties values of the tissue a region. This reconstruction process, using a hypothesized tumor location prior, can be repeated for any number of regions of image 300.

Images 301a-301e and 302 are the resulting images of the reconstruction process. Each image 301a-301e and 302 was produced by a reconstruction using a hypothesized tumor location prior within a different region. The region that were used for hypothesized tumor location prior is identified by an arrow from image 300 to images 301a-301e and 302. For images 301a-301e the hypothesized tumor location prior did not match the actual tumor location. For image 302 the hypothesized tumor location prior matched the actual tumor location. The different outcomes produced by the reconstruction when the hypothesized tumor location matches and when the hypothesized tumor location does not match is clearly illustrated in the different between images 301a-301e and image 302. Images 301a-301e are barely altered from image 310. Image 302 has drastically increased contrast with the tumor region experiencing an over ten fold increase in contrast from the surrounding background region. The method is also capable of producing over a fifty fold increase in contrast. The tumor location in image 302 is visible and easily detected. However, it is not practical to examine a reconstructed image for every hypothetical therefore to increase ease of use, reconstructed images 301a-301e and 302 can be compared against image 310 to determine the amount of contrast between the two images. If a tumor/inclusion is present a region the contrast between the reconstruction performed using hypothesized tumor location prior within that region and the original image should be elevated.

$\Delta\mu(r,r_0)$ is a set of 3D images associated with a particular hypothesized tumor location, $r_0$, resulting in a 6-dimensional image set. To facilitate the visualization of the optical contrast variations due to changes in the hypothesized tumor locations, a "metric function", $M(\cdot)$ is defined, to convert $\Delta\mu(r, r_0)$ to a single scalar, i.e. $\Delta\mu(r_0)=M(\Delta\mu(r,r_0))$.

The output of the metric function, M, becomes a 3D volumetric image, $\Delta\mu(r_0)$, that is only dependent on the hypothesized tumor location, $r_0$. There are a number of metric functions that can be used to collapse the 3D differential map into a scalar. One of the metric functions, referred to as $M_{max}$, is designed to extract the maximum changes before and after using the tumor prior for a given hypothesized tumor location, i.e. $M_{max}(\Delta\mu(r,r_0))=\max(\Delta\mu(r,r_0))$, $r \in G(r_0)$, where $G(r_0)$ denotes the search-grid that is centered at the assumed tumor location $r_0$. For a uniform 2D/3D search grid, the output of the above method is a pixelated or voxelated map.

Figure 4:
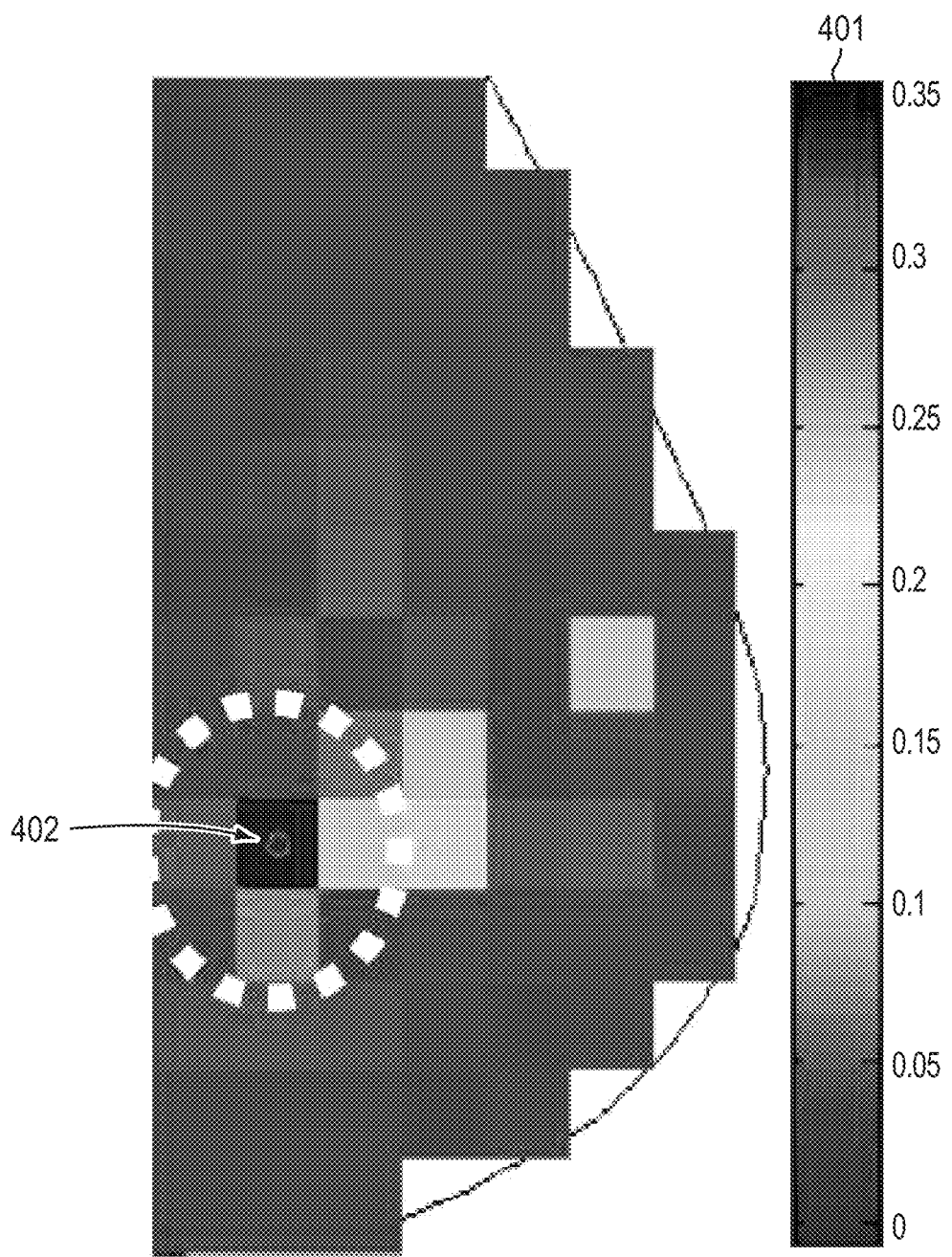
FIG. 4 shows the output of a metric function, referred to as $M_{max}$, when applied to the set of images shown in FIG. 3.

FIG. 4 shows the output of the metric functions, referred to as $M_{max}$, when applied to the set of images shown in FIG. 3. Each "pixel" in a region represents the contrast between the reconstruction performed using hypothesized tumor location prior within that region and the original image. The contrast is displayed by a heat map with key 401. The region 402 where the tumor is located is shown clearly in the map. The tumor region 402 as drastically increased contrast compared to both the non tumor regions as a whole and the surrounding tumors. This contrast variation, showing the tumor location, is created without any structural priors required by prior art methods.

Figure 5:
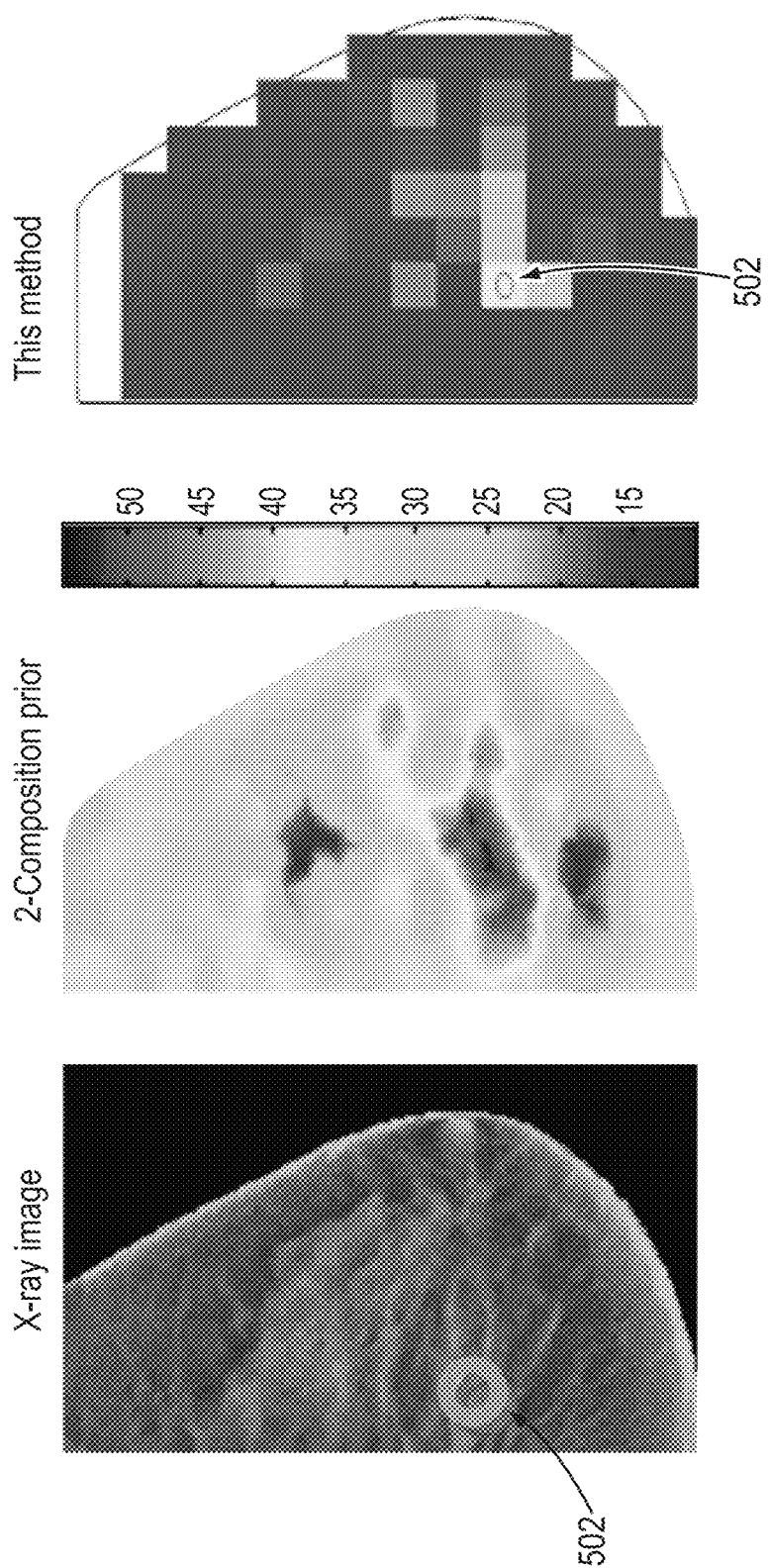
FIG. 5 is a comparison between an X-ray image, a prior art reconstruction method using two structural priors, and a reconstruction in accordance with this invention using only hypothesized tumor location.

FIG. 5 is a comparison between an X-ray image, a reconstruction method using two structural priors, and a reconstruction using only hypothesized tumor location. Tumor location 502 is clearly identified.

In addition to $M_{max}$, another metric function, $M_{map}$ can be used to bring more spatial details within each search grid. Instead of considering the entire tissue area, the contrast metric is defined using all nodes inside the search grid cell (denoted by $C_{i,j}$). The second metric, referred to as $M_{map}$, is represented by $M_{map}(\Delta\mu(r,r_0))=\Delta\mu(r,r_0)$, $r \in G(r_0)$. This will effectively "stitch" the patches of images for each search grid into a 3D image that covers the entire breast. Additional metric functions can be defined that extract other characteristics from the differential optical images, for example, calculating the variance or maximum difference in each search grid.

The contrast in the resulting images from the above methods highlights optical property changes due to the assumption that a tumor is located at a given location. Drastic changes can be observed near the true tumor location; in the regions where the tissue is normal, there are no significant changes.

Figure 6:
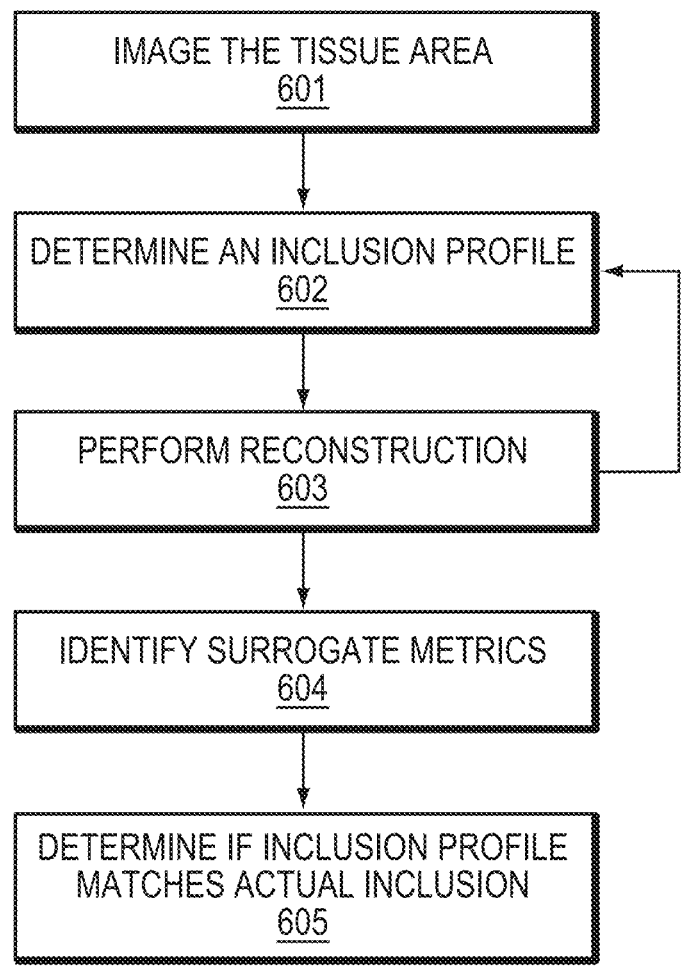
FIG. 6 is a flow chart that shows the steps of a method for characterizing an inclusion in accordance with the invention.

FIG. 6 is a flow chart that shows the steps of a method for characterizing an inclusion in accordance with the invention. The first step 601 is to image a tissue area. This imaging is accomplished with functional imaging that creates a map of physiological properties of the tissue area. The next step 602 is to determine an inclusion profile. The inclusion profile includes the hypothetical location of the inclusion and the known or suspected physiological properties of the inclusion. The inclusion profile may also include the hypothetical orientation, size, and/or shape of the inclusion. The inclusion profile may be based on stored data. Alternatively, the inclusion profile may be based on data inputted by a user.

Then a reconstruction is performed, step 603, with the inclusion profile mathematically incorporated. The reconstruction creates a new image of physiological properties of the tissue area. Steps 602 and 603 can be repeated for any amount of inclusion profiles allowing for multiple hypothetical locations, orientations, sizes, and/or shapes to be analyzed. In one embodiment, the tissue area is divided into regions and a reconstruction is performed for each region where the inclusion profile includes a hypothetical location within that region. From the reconstructed image(s) of physiological properties of the tissue area, surrogate metrics can be determined, step 604, the surrogate metrics characterize the reconstructed image's features. Surrogate metrics are chosen so that when the inclusion profile matches the actual inclusion, the surrogate metrics are dramatically altered compared to the original image created in step 601. Therefore, it is easy to determine if an inclusion profile matches the actual inclusion, step 605, based on comparison to the original image and/or other reconstructed images created from incorrect inclusion profiles. If the inclusion profile includes a hypothetical location, the inclusion profile that matches the actual inclusion will include the actual location of the inclusion.

Figure 7:
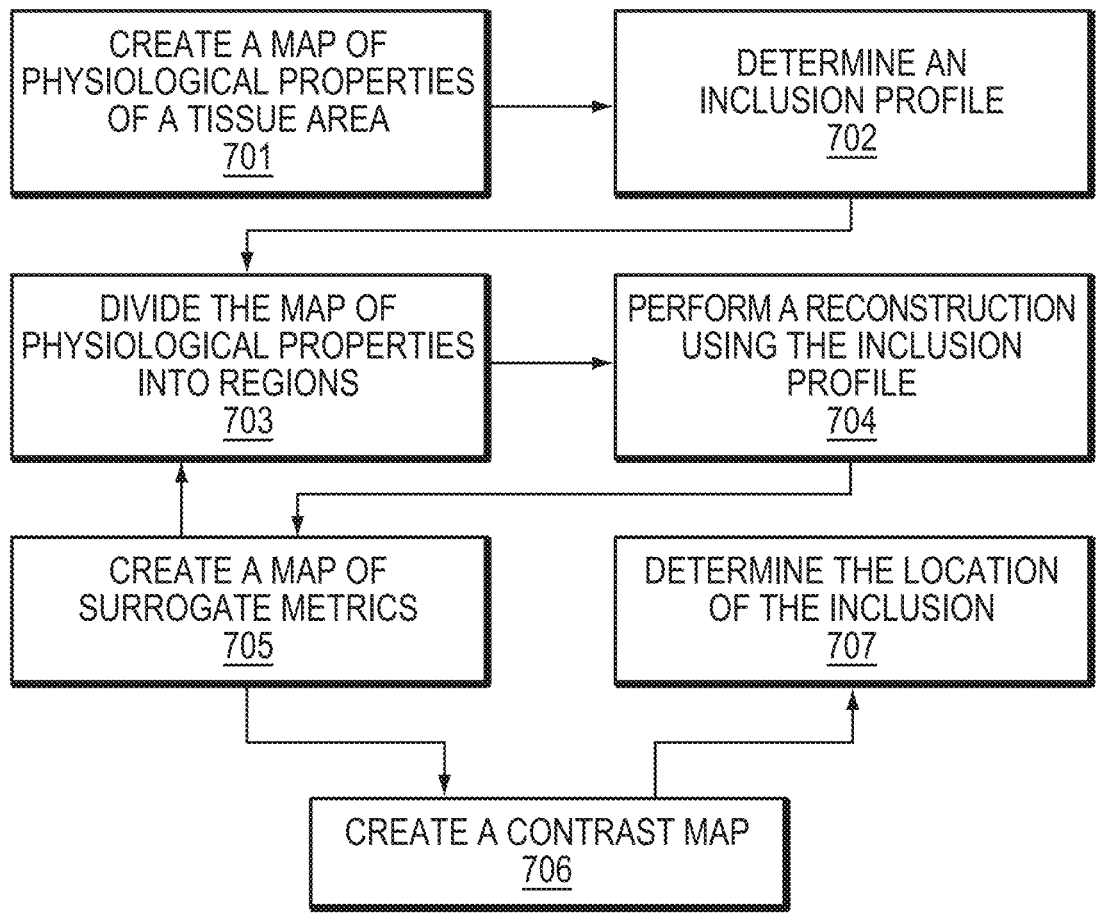
FIG. 7 is a flow chart that shows the steps of a method for locating an inclusion in accordance with the invention.

FIG. 7 is a flow chart that shows the steps of a method for locating an inclusion in accordance with the invention. The first step 701 is to create a map of physiological properties of the tissue area using a functional imaging technique. The next step 702 is to determine an inclusion profile. The inclusion profile is based upon either the known or suspected physiological properties of the inclusion which are distinct from the physiological properties of the background tissue. Step 703 is performed and the map of the physiological properties of the tissue area is divided into regions. Then in step 704, a reconstruction is performed on the map of physiological properties of the tissue area, created in step 701, using the inclusion profile as hypothesized known values of physiological properties of tissue with a region. Then, in step 705, a map of surrogate metrics, derived from the reconstruction, is created. Steps 704 and 705 are repeated for each region that was created in step 703. This creates, for each region, a map of surrogate metrics derived from a reconstruction where the inclusion profile was used as the hypothesized known values of the physiological properties of tissue within the region. When, a reconstruction is performed where the inclusion profile is placed at the location of the actual inclusion, the contrast of the surrogate metrics area are greatly increased relative to the original image compared to a reconstruction where the inclusion profile is placed at a location that does not have an actual inclusion. A contrast map can be created, step 706, that displays at each region the variation between the map of surrogate metrics and the original image from step 701. Finally, in step 707, the actual location of the inclusion is determined based up the maps of surrogate metrics and/or the contrast map.

Figure 8:
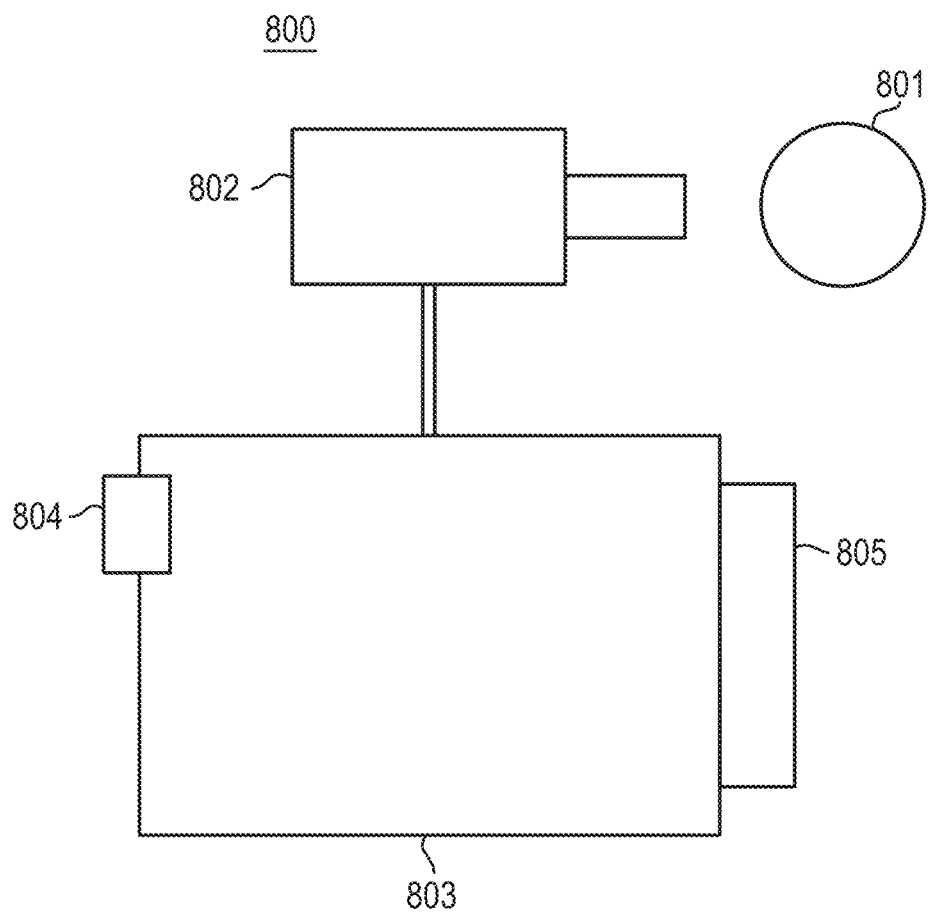
FIG. 8 is a schematic of a tissue abnormality detector in accordance with the invention.

FIG. 8 is a schematic of a tissue abnormality detector in accordance with the invention. Tissue abnormality detector 800 includes imaging system 802, analysis unit 803 and input 804. Imaging system 802 images tissue area 801. The imaging system may use function-oriented imaging techniques, such as positron emission tomography (PET), diffuse optical tomography (DOT), microwave tomography (MWT), and electrical impedance tomography (EIT), ultrasound elastography, or other similar techniques to create a map of physiological properties of a tissue area. In some embodiments, imaging system 802 is located on a personal portable device such as a cell phone. Tissue area 801 may be breast tissue, brain tissue or other regions of interest. Tissue area 801 is composed of a tissue abnormality and background tissue.

Analysis unit 803 is configured divide the map of physiological properties of the tissue area into regions and create, for each region, a map of surrogate metrics wherein the surrogate metrics derived from physiological properties of the tissue area calculated by applying a reconstruction using the abnormality profile as hypothesized known values of physiological properties of tissue within the region and wherein a region containing the tumor can be identified based upon the maps of surrogate metrics. Analysis unit 803 may be a covenantal computer with instructions programmed into its memory. Alternatively, analysis unit 803 may be a specialized device. Analysis unit 803 may be connected to imaging system 802 directly. Alternately, analysis unit 803 may be remote from imaging system 802.

Input 804 is configured to receive a tumor profile that includes physiological properties of the tumor, the physiological properties of the tumor being distinct from physiological properties of the background tissue. Input 804 may be part of analysis unit 803 as shown in FIG. 8. Alternatively, input 804 may be located on imaging system 802 or be remote from all other components of imaging system 800.

In some embodiments, imaging system 800 further include image output 805 that is configured to display a contrast map, the contrast map displaying, at each region, variation between the map of surrogate metrics of the tissue area created using the abnormality profile as the hypothesized known value of physiological properties of the tissue within the region and the map of physiological properties of the tissue area. Image output 805 may be located on analysis unit 803 as shown in FIG. 8. Alternatively, image output 805 may be located remotely from analysis unit 803.

Evaluating clinical breast imaging data with the one-composition approach, using only hypothesized tumor location prior, corroborates numerical breast phantom results. Tumor-negative breasts generate minimal contrast differential, although at a higher level than that found with three-composition priors. Malignant lesions were indicated in 26 out of 29 imaged breasts, as assessed with HbT and $\mu_s'$ differential (contrast) maps. In addition, the presence of some contrast altering inclusion is still indicated by non-baseline differential intensities even if the true tumor location is not perfectly localized.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of determining a location of an inclusion in a tissue area comprising:

creating, using a functional imaging technique, a map of physiological properties of the tissue area, wherein the tissue area is composed of the inclusion and background tissue;

determining an inclusion profile based upon physiological properties of the inclusion, the physiological properties of the inclusion being distinct from physiological properties of the background tissue;

dividing the map of physiological properties of the tissue area into regions;

creating, for each region, a map of surrogate metrics wherein the surrogate metrics are derived from physiological properties of the tissue area calculated by applying a reconstruction using the inclusion profile as hypothesized known values of physiological properties of tissue within the region;

determining the location of the inclusion based upon the maps of surrogate metrics.

2. The method of claim 1 wherein the functional technique is an ill-posed imaging technique.

3. The method of claim 2 wherein the ill-posed imaging technique is diffuse optical tomography.

4. The method of claim 1 wherein determining the location of the inclusion is accomplished without any structural images or structural information.

5. The method of claim 1 wherein the physiological properties of tissue area includes at least one of optical, dielectric, thermal, and mechanical characteristics.

6. The method of claim 1 wherein the physiological properties of tissue area includes at least one of oxyhemoglobin concentration, deoxyhemoglobin concentration, total hemoglobin concentration, oxygen saturation, water concentration, lipids concentration, absorption coefficient, and reduced scattering coefficient.

7. The method of claim 1 wherein determining the location of the inclusion includes creating a contrast map, the contrast map displaying, at each region, variation between the map of surrogate metrics of the tissue area derived by applying the reconstruction using the inclusion profile as the hypothesized known values of physiological properties of tissue within the region and the map of physiological properties of the tissue area.

8. The method of claim 7 wherein a region containing the inclusion has a variation over ten times greater than a region not containing the inclusion.

9. The method of claim 1 further comprising determining, based upon the maps of surrogate metrics of the tissue area, the shape, size, and orientation of the inclusion.

10. A tissue abnormality detector comprising:
- an imaging system that creates, using a functional imaging technique, a map of physiological properties of a tissue area, wherein the tissue area is composed of the abnormality and background tissue;
- an input configured to receive an abnormality profile that includes physiological properties of the abnormality, the physiological properties of the abnormality being distinct from physiological properties of the background tissue; and
- an analysis unit configured divide the map of physiological properties of the tissue area into regions and create, for each region, a map of surrogate metrics wherein the surrogate metrics are derived from physiological properties of the tissue area calculated by applying a reconstruction using the abnormality profile as hypothesized known values of physiological properties of tissue within the region and wherein a region containing the tumor can be identified based upon the maps of surrogate metrics.

11. The detector of claim 10 further composing an image output configured to integrate with a computer aided detection system to display the region containing the abnormality.

12. The detector of claim 11 wherein the image output is further configured to display a contrast map, the contrast map displaying, at each region, variation between the map of surrogate metrics of the tissue area created using the abnormality profile as the hypothesized known value of physiological properties of the tissue within the region and the map of physiological properties of the tissue area.

13. The detector of claim 10 wherein identifying the region containing the abnormality is accomplished without any structural images or structural priors.

14. The detector of claim 10 wherein the abnormality profile includes a shape of the abnormality.

15. The detector of claim 10 wherein the tissue area is breast tissue.

16. The detector of claim 10 wherein the tissue area is brain tissue.

17. The detector of claim 10 wherein the imaging system is located on a user's personal portable device.

18. The detector of claim 10 wherein the abnormality profile includes a size of the abnormality.

19. The detector of claim 10 wherein the abnormality is a tumor.

20. The detector of claim 19 wherein malignancy of the tumor can be determined using one or a combination of recovered contrast, shape, and size information.

* * * * *